United States Patent [19]

Fuchs et al.

[11] 4,215,141
[45] Jul. 29, 1980

[54] COMBATING INSECTS AND ACARIDS WITH 4,4,5,5-TETRACHLORO-2,2-DIMETHYL-SPIROPENTANE-1-CARBOXYLIC ACID 3-PHENOXY-BENZYL ESTERS

[75] Inventors: Rainer Fuchs, Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 41,222

[22] Filed: May 21, 1979

[30] Foreign Application Priority Data

Jun. 9, 1978 [DE] Fed. Rep. of Germany ....... 2825314

[51] Int. Cl.² .......................... A01N 9/20; A01N 9/24; C07C 69/74; C07C 121/66
[52] U.S. Cl. ................. 424/304; 260/465 D; 560/118; 424/305
[58] Field of Search ................... 260/465 D; 560/118; 424/304, 305

[56] References Cited

U.S. PATENT DOCUMENTS 3,950,535   4/1976   Davis et al. ................. 424/304

*Primary Examiner*—Dolph H. Torrence
*Attorney, Agent, or Firm*—Sprung, Felfe, Horn, Lynch & Kramer

[57] ABSTRACT

4,4,5,5-tetrachloro-2,2-dimethyl-spiropentane-1-carboxylic acid 3-phenoxy-benzyl esters of the formula

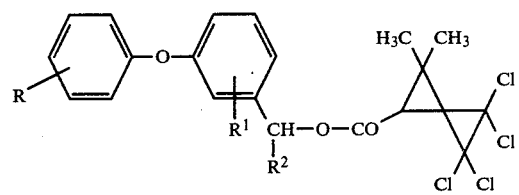

in which
R and $R^1$ each independently is hydrogen or halogen, and
$R^2$ is hydrogen, cyano or ethynyl,
which possess insecticidal and acaricidal properties.

9 Claims, No Drawings

COMBATING INSECTS AND ACARIDS WITH 4,4,5,5-TETRACHLORO-2,2-DIMETHYL-SPIROPENTANE-1-CARBOXYLIC ACID 3-PHENOXY-BENZYL ESTERS

The present invention relates to and has for its objects the provision of particular new 4,4,5,5-tetrachloro-2,2-dimethylspiropentane-1-carboxylic acid 3-phenoxybenzyl esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that phenoxybenzyl esters of spirocarboxylic acids, for example 2,2-dimethylspiro-(2,4)hepta-4,6-diene-1-carboxylic acid m-phenoxybenzyl ester, are suitable for combating insects (see DE-OS (German Published Specification) 2,605,828). However, the action of these compounds is not always satisfactory, especially when low concentrations and amounts are used.

The present invention now provides, as new compounds, the spiropentanecarboxylic acid esters of the general formula

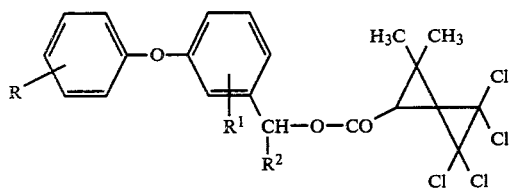

in which
R and $R^1$, which may be identical or different, each represent hydrogen or halogen and
$R^2$ represents hydrogen, cyano or ethynyl.

The general formula (I) includes the various isomers and mixtures thereof.

Preferably, R and $R^1$, which may be identical or different, each represent hydrogen or fluorine and $R^2$ represents hydrogen or cyano.

Specific examples of the compounds of the formula (I) which may be mentioned are: 4,4,5,5-tetrachloro-2,2-dimethylspiropentane-1-carboxylic acid 3-(4-fluoro-phenoxy)-benzyl ester, 3-(3-fluoro-phenoxy)-benzyl ester, 3-(2-fluorophenoxy)-benzyl ester, 4-fluoro-3-phenoxy-benzyl ester, 5-fluoro-3-phenoxy-benzyl ester, 6-fluoro-3-phenoxy-benzyl ester and 2-fluoro-3-phenoxy-benzyl ester, and 4,4,5,5-tetrachloro-2,2-dimethyl-spiropentane-1-carboxylic acid 3-(4-fluoro-phenoxy)-α-cyano-benzyl ester, 3-(3-fluoro-phenoxy)-α-cyano-benzyl ester, 3-(2-fluoro-phenoxy)-α-cyano-benzyl ester, 4-fluoro-3-phenoxy-α-cyano-benzyl ester, 5-fluoro-3-phenoxy-α-cyano-benzyl ester, 6-fluoro-3-phenoxy-α-cyano-benzyl ester and 2-fluoro-3-phenoxy-α-cyano-benzyl ester.

Surprisingly, the spiropentanecarboxylic acid esters according to the invention exhibit a better insecticidal action than the corresponding known products of analogous structure and the same type of action. The products according to the present invention thus represent a valuable enrichment of the art.

The invention also provides a process for the preparation of a spiropentanecarboxylic acid ester of the formula (I) in which 4,4,5,5-tetrachloro-2,2-dimethyl-spiropentanecarboxylic acid chloride, of the formula

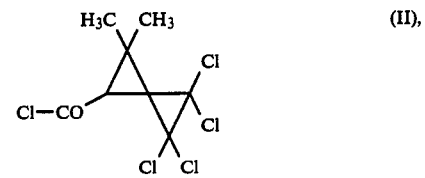

is reacted with a substituted phenoxybenzyl alcohol of the general formula

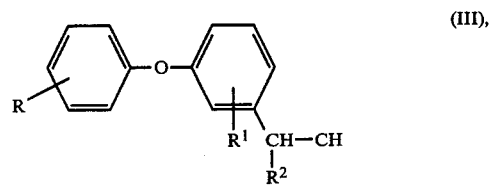

in which
R, $R^1$ and $R^2$ have the meanings stated above, if appropriate in the presence of an acid acceptor and if appropriate in the presence of a solvent or diluent.

If, for example, 4,4,5,5-tetrachloro-2,2-dimethylspiropentane-carboxylic acid chloride and 4-fluoro-3-(4-fluoro-phenoxy)-α-cyano-benzyl alcohol are used as starting substances, the course of the reaction can be outlined by the equation which follows:

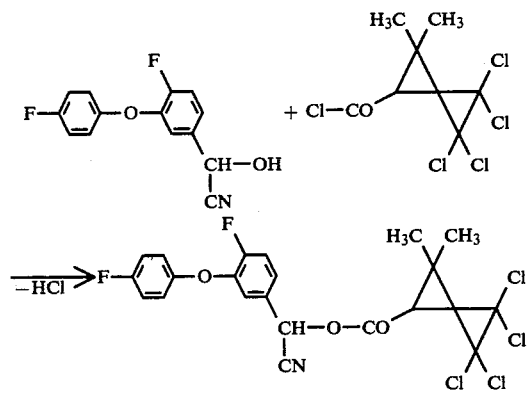

The 4,4,5,5-tetrachloro-2,2-dimethyl-spiropentanecarboxylic acid chloride (II) to be used as a starting material can be prepared by customary methods, starting from 4,4,5,5-tetrachloro-2,2-dimethyl-spiropentane-carboxylic acid methyl ester, which is known (see Chem. Ber. 107 (1974), 2760; and Liebigs Ann. Chem. 758 (1972), 148), for example by first preparing the corresponding carboxylic acid from the ester by boiling with aqueousalcoholic alkali metal hydroxide solution. Working up is effected, for example, by distilling off the alcohol, diluting the mixture with water, shaking it with methylene chloride and acidifying the aqueous phase with a strong acid, whereupon 4,4,5,5-tetrachloro-2,2-dimethyl-spiropentane-1-carboxylic acid is obtained as a crystalline product.

The acid chloride of the formula (II) can be prepared in a known manner from the acid mentioned, by reacting with a chlorinating agent, for example thionyl chloride, if appropriate using a diluent, for example carbon tetrachloride, at a temperature between 20° and 100° C., preferably between 50° and 90° C. It is appropriately purified by vacuum distillation.

The phenoxybenzyl alcohols of the formula (III) also to be used as starting compounds are known, and can be prepared by processes analogous to known processes (see DE-OS (German Published Specification) 2,621,433).

Specific examples of these compounds which may be mentioned are: 3-(4-fluoro-phenoxy)-, 3-(3-fluoro-phenoxy)- and 3-(2-fluoro-phenoxy)-benzyl alcohol, 4-fluoro-3-phenoxy-, 5-fluoro-3-phenoxy-, 6-fluoro-3-phenoxy- and 2-fluoro-3-phenoxy-benzyl alcohol, 3-(4-fluoro-phenoxy)-α-cyano-benzyl alcohol, 3-(3-fluoro-phenoxy)-α-cyano-benzyl alcohol, 3-(2-fluoro-phenoxy)-α-cyano-benzyl alcohol, 4-fluoro-3-phenoxy-α-cyano-benzyl alcohol, 5-fluoro-3-phenoxy-α-cyano-benzyl alcohol, 6-fluoro-3-phenoxy-α-cyano-benzyl alcohol and 2-fluoro-3-phenoxy-α-cyano-benzyl alcohol.

The process for the preparation of the spiropentanecarboxylic acid esters according to the invention is preferably carried out using a suitable solvent or diluent. Possible solvents or diluents are virtually all the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

All the customary acid-binding agents can be used as the acid acceptors. Acid acceptors which have proved particularly suitable are alkali metal carbonates and alcoholates, such as sodium carbonate and potassium carbonate sodium methylate and ethylate and potassium methylate and ethylate, and aliphatic, aromatic or heterocyclic amines, for example triethylamine, trimethylamine, dimethylaniline, dimethylbenzylamine and pyridine.

The reaction temperature can be varied within a substantial range. In general, the reaction is carried out between 0° and 100° C., preferably at from 15° to 40° C. The reaction is in general carried out under normal pressure.

The starting substances are usually employed in equimolar amounts for carrying out the process according to the invention. An excess of one or the other of the reactants brings no substantial advantages. In general, the reaction is carried out in a suitable diluent in the presence of an acid acceptor and the reaction mixture is stirred at the required temperature for several hours.

Thereafter, the reaction mixture is cooled, poured into water and extracted by shaking with an organic solvent, for example toluene. The organic phase is then worked up in the customary manner, by washing and drying and distilling off the solvent.

The new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. The refractive index is used for their characterization.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example Geophilus carpophagus and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratoriodes, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix, Pemphigus* spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana,*

*Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis,* Atomaria spp., *Oryzaephilus surinamensis, Anthonomus,* spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., Tenebrio molitor, Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* And *Tipula paludosa;* from the oder of the Siphonaptera, for example *Xenopsylla cheopis* and *Ceratophyllus* spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example, by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods, especially insects or acarids, which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

Preparation of the novel compounds is shown in the following illustrative examples:

EXAMPLE 1

(A)

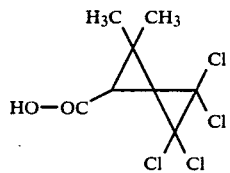

22.95 g (0.075 mol) of 4,4,5,5-tetrachloro-2,2-dimethyl-spiropentane-1-carboxylic acid methyl ester were dissolved in 100 ml of ethanol and, after adding 6 g of sodium hydroxide, dissolved in 100 ml of water, the mixture was heated under reflux for 4 hours. The ethanol was then stripped off in vacuo, 100 ml of water were added to the residue and the mixture was extracted with 200 ml of methylene chloride. The aqueous phase was acidified with concentrated hydrochloric acid and the solid which precipitated was filtered off, washed with water and dried. 13 g (62.4% of theory) of 4,4,5,5-tetrachloro-2,2-dimethyl-spiropentane-1-carboxylic acid were obtained as a colorless solid with a melting point of 198°–199° C.

(B)

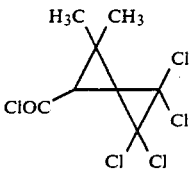

13 g (0.0467 mol) of 4,4,5,5-tetrachloro-2,2-dimethyl-1-spiropentane-1-carboxylic acid were dissolved in 200 ml of carbon tetrachloride and the solution was heated under reflux, together with 50 ml of thionyl chloride, for 3 hours. Excess thionyl chloride and carbon tetrachloride were then stripped off in vacuo and the residue was distilled in vacuo. 8.1 g (58.5% of theory) of 4,4,5,5-tetrachloro-2,2-dimethyl-spiropentane-1-carboxylic acid chloride were obtained as a colorless liquid with a boiling point of 120° C./10 mm Hg.

(C)

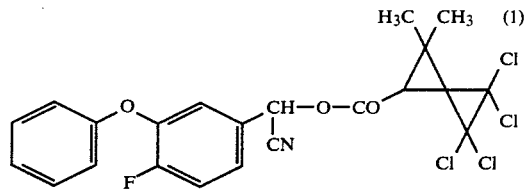 (1)

7.5 g (0.025 mol) of 4,4,5,5-tetrachloro-2,2-dimethyl-spiropentane-1-carboxylic acid chloride and 6.1 g (0.025 mol) of 3-phenoxy-4-fluoro-α-cyano-benzyl alcohol were dissolved in 100 ml of anhydrous toluene, and 2.2 g of pyridine, dissolved in 50 ml of anhydrous toluene, were added dropwise at 20°–25° C., while stirring. The reaction mixture was then stirred at 25° C. for a further 3 hours. It was poured into 150 ml of water and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 10.2 g (81.1% of theory) of 4,4,5,5-tetrachloro-2,2-dimethyl-spiropentane-1-carboxylic acid 3-phenoxy-4-fluoro-α-cyanobenzyl ester were obtained as a yellow oil with the refractive index $n_D^{25}$: 1.5653.

The following compounds were obtained analogously:

| Compound 2 | | Yield: | Refractive index |
|---|---|---|---|
| 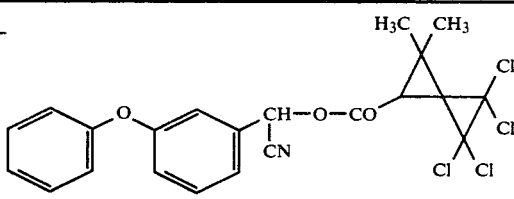 | | 72.7% of theory | $n_D^{25}$: 1.5641 |

| | | |
|---|---|---|
| Compound 3 | 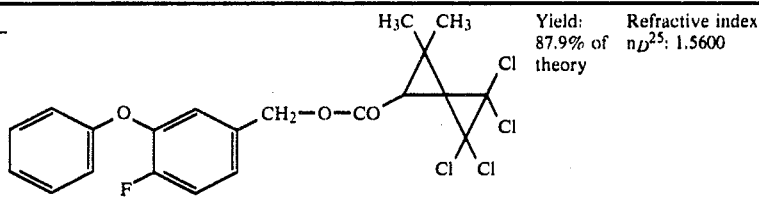 | Yield: 87.9% of theory    Refractive index $n_D^{25}$: 1.5600 |
| Compound 4 | 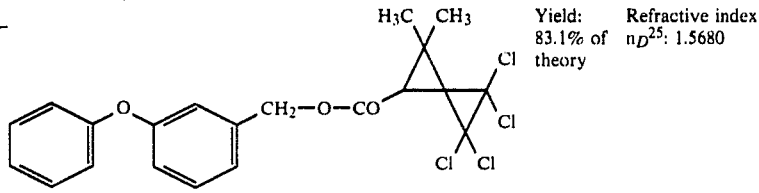 | Yield: 83.1% of theory    Refractive index $n_D^{25}$: 1.5680 |

The insecticidal and acaricidal activity of the compounds of this invention is illustrated by the following examples wherein the compounds according to the present invention are each identified by the number (given in brackets) from Example 1.

EXAMPLE 2

Laphygma test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all of the caterpillars had been killed whereas 0% indicated that none of the caterpillars had been killed.

In this test, for example, compound (1) showed a superior activity compared to the prior art.

EXAMPLE 3

Myzus test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infected with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, compound (1) showed a superior activity compared to the prior art.

EXAMPLE 4

Test with parasitic fly larvae

Emulsifier: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction in % was determined. 100% meant that all of the larvae had been killed and 0% meant that none of the larvae had been killed.

In this test, for example, compound (1) showed a superior activity compared to the prior art.

EXAMPLE 5

Test with parasitic adult cattle ticks (*Boophilus microplus* res.)

Solvent: Alkylaryl polyglycol ether

To produce a suitable preparation of active compound, the active substance in question was mixed with the stated solvent in the ratio of 1:2, and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction in percent was determined, 100% meaning that all of the ticks had been killed and 0% that none of the ticks had been killed.

In this test, for example, compound (1) showed a superior activity compared to the prior art.

It will be appreciated that the instant specification and examples are set forth by way of illustration and not limitation, and that various modifications and changes may be made without departing from the spirit and scope of the present invention.

What is claimed is:

1. A 4,4,5,5-tetrachloro-2,2-dimethyl-spiropentane-1-carboxylic acid 3-phenoxy-benzyl ester of the formula

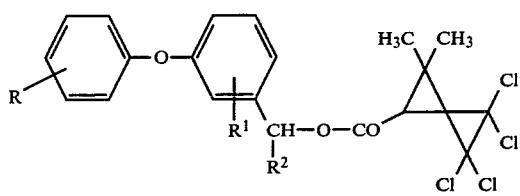

in which

R and $R^1$ each independently is hydrogen or halogen, and $R^2$ is hydrogen, cyano or ethynyl.

2. A compound according to claim 1, in which

R and $R^1$ each independently is hydrogen or fluorine, and $R^2$ is hydrogen or cyano.

3. A compound according to claim 1, wherein such compound is 4,4,5,5-tetrachloro-2,2-dimethyl-spiropentane-1-carboxylic acid 3-phenoxy-4-fluoro-α-cyano-benzyl ester of the formula

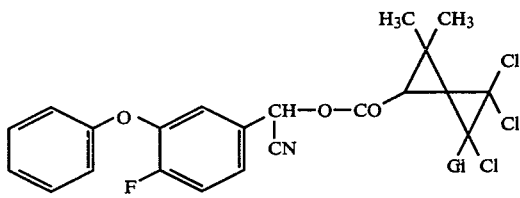

4. A compound according to claim 1, wherein said compound is 4,4,5,5-tetrachloro-2,2-dimethyl-spiropentane-1-carboxylic acid 3-phenoxy-α-cyano-benzyl ester of the formula

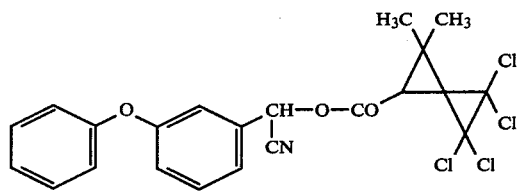

5. A compound according to claim 1, wherein said compound is 4,4,5,5-tetrachloro-2,2-dimethyl-spiropentane-1-carboxylic acid 3-phenoxy-4-fluoro-benzyl ester of the formula

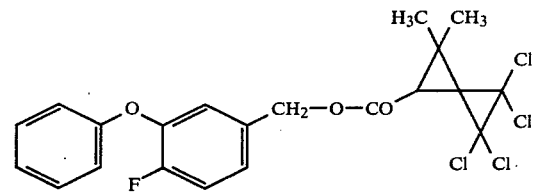

6. A compound according to claim 1, wherein such compound is 4,4,5,5-tetrachloro-2,2-dimethyl-spiropentane-1-carboxylic acid 3-phenoxy-benzyl ester of the formula

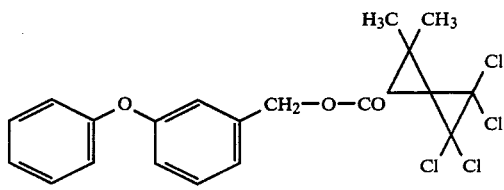

7. An arthropodicidal composition containing as active ingredient an arthropodicidally effective amount of a compound according to claim 1 in admixture with a diluent.

8. A method of combating arthropods which comprises applying to the arthopods, or to a habitat thereof, an arthropodicidally effective amount of a compound according to claim 1.

9. The method according to claim 8, wherein the compound is 4,4,5,5-tetrachloro-2,2-dimethyl-spiropentane-1-carboxylic acid 3-phenoxy-4-fluoro-α-cyanobenzyl ester, 4,4,5,5-tetrachloro-2,2-dimethyl-spiropentane-1-carboxylic acid 3-phenoxy-α-cyano-benzyl ester, 4,4,5,5-tetrachloro-2,2-dimethyl-spiropentane-1-carboxylic acid 3-phenoxy-4-fluoro-benzyl ester, or 4,4,5,5-tetrachloro-2,2-dimethyl-spiropentane-1-carboxylic acid 3-phenoxy-benzyl ester, and is applied to a domesticated animal thereby to free and protect the animal from parasitical insects and acarids.

* * * * *